United States Patent [19]

Lewis

[11] 3,930,945
[45] Jan. 6, 1976

[54] UROKINASE PRODUCTION
[75] Inventor: L. James Lewis, Iowa City, Iowa
[73] Assignee: Abbott Laboratories, North Chicago, Ill.
[22] Filed: Mar. 31, 1975
[21] Appl. No.: 564,966

[52] U.S. Cl. .............................. 195/1.7; 195/66 B
[51] Int. Cl.² ..................... C12K 9/00; C07G 7/026
[58] Field of Search ............... 195/65, 66 B, 1.7, 1.8

[56] References Cited
OTHER PUBLICATIONS
Bernik et al., Journal of Clinical Investigation, Vol. 52, pp. 823–834, Apr. 1973.

Chemical Abstracts, Vol. 77, 136739v (1972).

Primary Examiner—Lionel M. Shapiro
Attorney, Agent, or Firm—Paul D. Burgauer; Robert L. Niblack

[57] ABSTRACT

The addition of specified amounts of glycine to the production medium for urokinase using live cells increases the production of urokinase by 50 – 600%.

2 Claims, No Drawings

UROKINASE PRODUCTION

DETAILED DESCRIPTION OF THE INVENTION

Urokinase has been known since about 1951 as a substance capable of effecting the transformation of plasminogen to plasmin. As such, it has found use as an activator to promote the lysis of blood clots. Unfortunately, a single dose capable of dissolving a blood clot requires a rather large amount of urokinase which, up to 1962, was primarily extracted from urine. Since that time, cultures of kidney cells from various animals have been used for producing urokinase by culturing them in a proper medium. Urokinase obtained in this fashion is immunologically indistinguishable from the urinary urokinase used earlier. Kidney cells can be propagated on a large scale before they are used for producing urokinase, but even then, urokinase production is costly and limited by the space required for this operation.

In order to supply sufficient amounts of the drug for use in the field of human blood clot therapy, the cell culture, the media used to grow the cell culture and the method for propagating these cells have been experimented with to optimize urokinase production. Unfortunately, the success so far has been rather limited and the amount of urokinase produced has been sufficient only to run experimental studies. More particularly, urokinase production per culture surface area and time must be increased to make this fibrinolytic enzyme an available tool for human clot treatment.

It is therefore an object of this invention to increase the production of urokinase for propagated cell cultures. It is a particular object of this invention to improve the yield of urokinase from a cell culture to the extent of much greater yield in quantity without adversely affecting the quality of the material.

These and other objects are accomplished by the process of producing urokinase from a contiguous kidney cell culture in an organic nutrient medium containing between 0.3 and 1.2% glycine.

Nutrient media have been known and described for considerable periods of time. They have been used in individual bottles as well as in petri dishes, rose chambers or the culture equipment known as the mass tissue culture propagator (MTCP) which enables the production of urokinase from kidney cells on a large scale. Use of the MTCP eliminates some of the disadvantages involved with culturing mammalian cells in bottles, primarily the need for an extremely large number of bottles for volume production and the logistical problems associated with the use of such large number of bottles. The MTCP also provides a means for maintaining the same conditions for all the cells in the various individual layers and enables uniformity in pH, dissolved oxygen and dissolved carbon dioxide throughout the medium. The MTCP consists essentially of a glass vessel containing a number of shallow glass plates or dishes stacked on top of one another. This propagator is then filled to just cover the plates with medium containing the desired number of cells. The cells attach to and grow on the plates. A carbon dioxide/air mixture is introduced and continuously supplied to provide oxygen and pH control of the known, usually bicarbonate buffered, medium. If desired, mechanical means can be provided to circulate the medium over the cell culture.

In production runs, the cells are first grown to confluency in the cell growth medium; the growth medium is then completely replaced by a second medium suitable for the production of urokinase by the cells so grown. It is to this latter medium that the present invention is directed.

In a general embodiment of the present invention, cells known to produce urokinase are grown in plastic or glass flasks; they are then planted in an appropriate growth medium and incubated at 37° C. in a closed system after gassing the latter with carbon dioxide to a pH of 7.2. Upon reaching confluency, the cells are washed with buffered saline which liquor is then replaced by a suitable maintenance medium which contains various additives necessary for maintaining these cells and their production of urokinase.

While both the growing of the cells to confluency and maintenance of their production capabilities have been described in the literature, it has now been found that this urokinase production can be increased significantly by adding to the medium between 0.3 and 1.2 parts by weight of glycine per 100 parts by volume of medium. Ordinarily, after about 4 – 5 weeks, the culture has produced a commercial optimum of urokinase. By commercial optimum is meant that the amount of urokinase obtained is not necessarily the maximum obtainable but an amount which reduces the efficiency for further urokinase production to the point where it becomes more attractive to start with a fresh batch of monolayered (contiguous) growth culture.

In order to illustrate the advantage obtained by the present invention, reference is made to the following specific examples which, however, are not meant to limit the invention in any respect.

EXAMPLE 1

Human embryonic kidney cells grown in 75 mm. Falcon flasks are planted at $5 \times 10^5$ cells in 40 ml. of the nutrient medium consisting of Parker's medium, described in Grand Island's Biological catalog (GIBCO) and containing $1 \times$ BME (basal minimal essential vitamins and amino acids, described ibid.) as well as 10% by volume of fetal calf serum. The flasks are incubated at 37° C. in a closed system after gassing them with carbon dioxide to a pH of 7.2. When confluency or a contiguous monolayer of the cells is obtained, the cells are washed with a 0.8% aqueous NaCl solution buffered with phosphate to a pH of 7.4.

The wash liquor is now replaced by the maintenance medium consisting of 0.5 weight % of lactalbumin hydrolysate, various amounts (weight by volume) of human serum albumin (HSA) and 0.1 weight % of glucose in 0.8% of Earle's balanced salt solution and containing various amounts (by weight) of glycine (Gly) as shown below and 0.8 g/lt. of sodium bicarbonate. The results obtained are listed as urokinase titers per ml. on the days indicated in Table I.

TABLE I

| Additive | Day 10 | Day 19 | Day 33 | Day 42 |
| --- | --- | --- | --- | --- |
| 0.5% HSA | 86 | 195 | 335 | 443 |
| 0.5% HSA + 0.6% Gly | 129 | 264 | 498 | 647 |
| 0.1% HSA | 80 | 179 | 275 | 396 |
| 0.1% HSA + 0.6% Gly | 145 | 276 | 539 | 671 |
| 0.05% HSA | 96 | 164 | 309 | 443 |
| 0.05% HSA + 0.6% Gly | 112 | 204 | 362 | 535 |
| 0.05% HSA | 80 | 157 | 297 | 427 |
| 0.05% HSA + 0.6% Gly | 116 | 213 | 408 | 536 |
| Average Increase | 52% | 38% | 48% | 40% |

EXAMPLE 2

In a further experiment using the same kidney cell growth and wash procedure as above and using 5 cell propagation flasks for each level of additives for testing urokinase production, the maintenance medium consists of the same basic nutrient but contains 1 g./lt. of glucose and varied amounts of glycine. Table II shows the effects (averaged over the 5 flasks) analyzed as urokinase CTA units/ml. after several days. All media contain 0.1 weight % human serum albumin per volume.

TABLE II

| | | | |
|---|---|---|---|
| a) | Above medium + 0.6% Gly: | 567 after 27 days | 700 after 34 days |
| | Above medium + 0.9% Gly: | 688 after 27 days | 755 after 34 days |
| | Above medium + 1.2% Gly: | 740 after 27 days | 774 after 34 days |
| b) | Above medium + 0.6% Gly: | 357 after 29 days | 512 after 36 days |
| | Above medium + 0.9% Gly: | 377 after 29 days | 579 after 36 days |
| | Above medium + 1.2% Gly: | 589 after 29 days | 721 after 36 days |
| c) | Above medium + 0.6% Gly: | 302 after 28 days | 554 after 36 days |
| | Above medium + 0.9% Gly: | 449 after 28 days | 651 after 36 days |
| d) | Above medium + 0.6% Gly: | 652 after 27 days | 963 after 34 days |
| | Above medium + 0.9% Gly: | 714 after 27 days | 1008 after 34 days |
| | Above medium + 1.2% Gly: | 820 after 27 days | 1155 after 34 days |

EXAMPLE 3

While the above experiments clearly show the improvements in urokinase production by the addition of various amounts of glycine to the maintenance medium, this example shows the particular benefit of the glycine addition to all cultures that are considered marginal as far as their urokinase production ability is concerned (producing 400 or less CTA units of urokinase in 30 days). The same medium as in Example 2 is used.

A culture producing 350 units in 30 days with 0.6% glycine produces 584 units with 1.0% glycine and 598 units with 1.2% glycine.

A culture producing 549 units with 0.6% glycine in 35 days produces 748 units with 0.9% glycine and 1011 units with 1.2% glycine.

Three cultures (a, b and c) analyzed after 35 days with 0.6%, 0.9% and 1.2% glycine, respectively, showed the following CTA units of urokinase: (a) 473 – 793 – 1011; (b) 265 – 469 – 449; (c) 309 – 547 – 606. Two other cultures (d and e) analyzed after 34 days showed: (d) 265 – 479 – 661; (e) 265 – 400 – 633 CTA units of urokinase.

EXAMPLE 4

In a further experiment, carried out in the fashion described in Example 1, the beneficial effect on urokinase yield was tested. The results obtained in 3, 4 and 5 weeks' time are shown in Table III below. The results again are expressed in CTA units/ml. of urokinase.

TABLE III

| Days | 21 | 28 | 35 |
|---|---|---|---|
| 0% glycine | 59 | 92 | 116 |
| 3.0% glycine | 104 | 157 | 158 |
| 6.0% glycine | 170 | 264 | 315 |
| 7.0% glycine | 234 | 329 | 330 |
| 8.0% glycine | 303 | 446 | 419 |
| 9.0% glycine | 436 | 487 | 483 |

It will be seen from the above examples that the effect of glycine is very pronounced and enables the use of only marginal cell cultures for the propagation of urokinase but even with optimum cell cultures, large increases in production are observed. These increases range between 50 and 600% of the norm expected from the same nutrient or maintenance medium that does not have the benefit of the added glycine.

It is interesting to note and surprising to discover that a particular amino acid in a particular range produces the outstanding and unexpected results demonstrated above. Glycine is the simplest and most abundant amino acid and even though minor proportion of certain amino acids may already be part of amino acid supplements ordinarily used in production media for kidney cells, the amounts used in the present invention are in the range of 100-fold of amounts ordinarily used. It is also surprising to find that unlimited amounts of glycine are not useful and that the optimum amount of the supplement is in the range of between 0.3 – 1.2% by volume of the nutrient production medium. Amounts below 0.3% show very little but still commercially useful increases in urokinase production while amounts above 1.2% by volume tend to be detrimental to that end. It is also surprising to find that the simplest existing amino acid has this profound effect on the production of urokinase. Other amino acids used in quantities comparable to those used in the present invention have no or sometimes even opposite effects on urokinase production.

As pointed out above, best results are obtained when a contiguous monolayered structure of cells adhered to a solid surface is used for the production of urokinase. Such monolayered structures have been used by earlier investigators and have been described in the literature. Optimum temperature for the above process of producing urokinase is 37° C. ± 0.5°; at temperatures below this range, urokinase production is slower than what can be achieved and at temperatures above the range indicated, the danger of damaging the cells which produce the urokinase is increased to the point where production is jeopardized.

As will be recognized by those skilled in the art of maintaining live cells in a nutrient medium, the above-demonstrated beneficial effect can be achieved with any kind of nutrient medium used for kidney cells. Such media may contain various proportions of minerals and/or vitamins, buffers, etc. and various concentrations of ingredients such as the commonly used Earle's balanced salt solution, sodium bicarbonate and other additives commonly used for nutrients for the above purpose.

What is claimed is:

1. The process of producing urokinase from a contiguous culture of live kidney cells in an aqueous nutrient medium containing, in addition to the usual cell culture maintenance additives, between 0.3 and 1.2 parts by weight of glycine per 100 parts by volume of said nutrient.

2. The process of claim 1 wherein said glycine is used in an amount of between 0.6 and 1.2 parts by weight.

* * * * *